United States Patent [19]

Berenter

[11] Patent Number: 4,900,732

[45] Date of Patent: Feb. 13, 1990

[54] METHOD OF TREATING AMERICAN AND ORIENTAL COCKROACHES

[76] Inventor: Allen Berenter, 700 Sligo Ave., Silver Spring, Md. 20910

[21] Appl. No.: 477,598

[22] Filed: Mar. 28, 1983

Related U.S. Application Data

[63] Continuation of Ser. No. 114,567, Jan. 23, 1980, which is a continuation-in-part of Ser. No. 58,942, Jul. 19, 1989, abandoned.

[51] Int. Cl.$^4$ .................. A01N 29/04; A01N 57/00
[52] U.S. Cl. .................................. 514/122; 514/747; 514/755
[58] Field of Search .................. 514/122, 747, 755; 424/200

[56] References Cited

U.S. PATENT DOCUMENTS

| | | | |
|---|---|---|---|
| 3,006,809 | 10/1961 | Gershon | 424/200 |
| 3,761,589 | 9/1973 | Balassa | 424/200 |
| 3,790,582 | 2/1974 | Demozay | 260/294 K |
| 4,012,506 | 3/1977 | Balke et al. | 424/200 |

OTHER PUBLICATIONS

Chem. Abst. 76, 42747(y) (1972)—Flynn et al.
Chem. Abst. 77, 136,245(f) (1972)—Sterling et al.
Chem. Abst. 78, 120169(u) (1973)—Collins.
Chem. Abst. 81, 34468(w) (1974)—Gupta et al.
Chem. Abst. 82, 150472(n) (1975)—Burden et al.
Chemical Abstracts, vol. 85, 1976, Abstract No. 85:29507m.
"Cockrochaces—How to Control Them", Leaflet No. 430, US Dept. of Agriculture, Revised Nov. 1971.
"Cockroaches—How to Control Them", Leaflet No. 430, US Dept. of Agriculture, Revised Dec. 1978.
"Roaches Impervious to Most Commercial Baits, Traps and Sprays, Study Concludes", Lorraine Bennett, Los Angeles Times, Apr. 4, 1980, Part IV, p. 11.

*Primary Examiner*—Douglas W. Robinson
*Attorney, Agent, or Firm*—Ronald P. Kananen; Clifton E. McCann

[57] ABSTRACT

Infestation of cockroaches in buildings and houses are treated and effectively eliminated by determining the location of the eggs or the young, immature insects and treating them with a suitable insecticide before the insects emerge and begin to migrate to other areas. The treatment can also be applied to mature roaches in these areas before they lay their eggs. Frequently the places where the young roaches develop or hatch is in the foundations and walls of buildings and under concrete slabs where sewer or water lines occur and other damp or humid areas. A particularly effective insecticide has been found to be a dilute solution of O, O-diethyl-O-(2-isopropyl-6- methyl-4 pyrimidinyl phosphorothioate which is used to saturate the area being treated.

5 Claims, No Drawings

METHOD OF TREATING AMERICAN AND ORIENTAL COCKROACHES

This application is a continuation of Ser. No. 114,567, filed Jan. 23, 1980, now abandoned, which is a continuation-in-part of Ser. No. 058,942, filed July 19, 1979, now abandoned.

BACKGROUND OF THE INVENTION

The present invention is directed to a method for controlling and eliminating infestations of cockroaches in habitations such as homes and buildings.

The common cockroach is one of the oldest, most persistent, and wide-spread of all of the insect pests which have vexed mankind throughout his history. In fact, this pest has a durability which has permitted it to persist in its present day forms from prehistoric times and, in spite of advances which have been made in the science of pest control, the cockroach still remains a serious problem in many areas of the world.

Although there are approximately 55 different species of cockroaches in the United States alone, only five or so of these species actually present any serious problem insofar as infestation of buildings is concerned. Of these five species, three which are particularly troublesome are the American cockroach (*Periplaneta americana*), the Oriental cockroach (*Blatta orientalis*) and the Australian cockroach (*Pariplaneta australasiae*).

Although generally the presence of roaches in buildings or other dwellings is encouraged by poor/hygienic practices, roaches may appear in even relatively clean or sanitary locations. Cockroaches may, for example, enter a house from outdoors in infested containers from other buildings or adjoining habitats. Therefore, the sealing of cracks and proper disposal of containers as well as waste food are all important in preventing or controlling infestations of these pests.

Once the cockroaches have become established in a dwelling or other building, however, it becomes more difficult to eliminate them. Infestations of roaches have in the past been controlled by applying insecticides in the form of sprays and dusts along baseboards, under cupboards and similar areas where it is assumed the roaches will migrate at night in search of food. Such treatments, however, are primarily directed to eliminating mature or adult roaches as they forage for food and therefore, only serve to temporarily control the infestation since the roaches may continue to lay eggs and young roaches are free to continue to develop in their more remote areas of habitation.

Accordingly, it is an object of the present invention to provide an effective method for controlling and eliminating infestations of cockroaches by attacking the roaches during the early stages of their development or before they hatch.

SUMMARY OF THE INVENTION

According to the present invention, infestations of the cockroaches are effectively eliminated by first locating the areas where the eggs are laid and where the young roaches develop from these eggs prior to the roach reaching a size and maturity where it begins an exodus from its area of development into other sections of the infested building. Once the area of development is located, the roaches are attacked with a suitable pesticide by saturating the area with the pesticide in sufficient quantity to eliminate the young, immature roaches present.

It is a further aspect of the present invention that it has been found that a distinguishing characteristic of certain types of cockroaches is that they pass through an early developmental stage prior to maturity and before beginning migrations to other areas of the infested building.

These types of roaches, which are typified by the American Roach (*Pariplaneta americana*), the Oriental Roach (*Blatta orientalis*) and the Australian Roach (*Pariplaneta australasiae*), have the additional significant characteristic that they will not breed, lay eggs or develop outside the original habitat of their early development.

By attacking the roach with effective quantities of pesticide at this early developmental stage or adult stage, in the initial habitat, rather than attempting to poison it during its latter post-migratory stage, it has been found that infestations of these insects cannot only be controlled but effectively eliminated.

Although various areas may exist in building structures depending to some extent upon the particular structure in question, in general the young, immature cockroach to which the invention is directed has been found to inhabit hollow recesses in the lower portions of the foundations and walls of buildings and habitats. For example, in structures built of hollow concrete block, the hollow recesses in the block form ideal and typical areas of habitation for these roaches prior to their migrating to other parts of the building in their mature stage. Additionally, such areas of habitation may occur in recesses under concrete slabs, and especially under slabs on grade where sewer or water pipes are located or in the area of incinerators, which have been converted into trash compactors or trash rooms. Access to such areas may be obtained, for example, by drilling holes in the blocks, walls, slab or other portions of the foundation.

Once the areas of roach inhabitations are located and access holes drilled, each space is saturated according to the present invention with about a 0.5 to 2 percent solution or aqueous emulsion of suitable insecticide. Typically, an area of about one square foot will be saturated with 1/10 to ¾ of a gallon of this insecticide solution or more preferably 1/10 to ½ gallon per square foot.

Various insecticides have in the past been employed for the control of insect infestation and particularly cockroach infestation. Typical of these insecticides which the prior art has employed are Chlordane (octachloro-4,7-methano-tetrahydroindane), Lindane (gamma isomer of benzene hexachloride), and Malathion (0,0 dimethyl dithiophosphate of diethyl mercaptosuccinate). The insecticides, which in the past have generally been spread around base-boards or under cabinets have been employed as dusts, in oil or other hydrocarbon solvents, or in the form of an aqueous emulsion of the insecticide.

Most preferred according to the present invention, however, is the insecticide 0,0-diethyl-0 (2-isopropyl-6 methyl-4 pyrimidinyl) phosphorothioate which is sold commercially as Diazinon or Spectracide. Typically, this insecticide is available in about a 48 percent solution of the insecticide in a hydrocarbon solvent. This solution is conveniently mixed with a suitable amount of water to make an aqueous emulsion having a strength of about 0.5 to 2 percent and most preferably a 0.5 to 1 percent solution based upon the actual amount of diazinon in the total aqueous solution.

The required amount of insecticide is introduced into each structural cavity either through the hole which has been drilled or any natural crevice which may be present by means typically of a stream or any other suitable means of application. Depending on the extent of infestation and its duration prior to treatment, once the infested area has been thoroughly treated, it may be anticipated that no new roaches will appear in the dwelling for an indefinite period of time unless of course new roaches gain access from outside the dwelling structure. In cases of acute or prolonged infestation, a second application, 1–3 months after the first may be desirable. Any adult roaches which may have migrated to other sections of the dwelling prior to treatment of the area of development of the infantile roaches will soon die off and will not lay eggs or reproduce in areas of the building other than the area which has been treated.

EXAMPLE 1

Infestations of Oriental cockroaches were eliminated effectively by drilling individual holes in hollow cinder blocks which form the foundation walls of a building used for an appartment. One hole drilled into each such cavity in a cinder block and about one gallon of a one half percent aqueous emulsion of diazinon was injected into the cavity. Subsequent to this treatment, no further roach infestations were observed in the building.

EXAMPLE 2

The procedures of Example 1 were repeated except that the area treated was one with known roach infestation for a three year period. Following the initial application of insecticide, a second similar treatment was applied 45 days later. No recurrence of the roach infestation was noted for nine months.

I claim:

1. A method for treating a building having an infestation of cockroaches selected from the species *Periplaneta americana, Periplaneta australasiae,* and *Blatta orientalis,* said species being characterized in that a first habitat of these species during early development and reproduction is different from a second habitat of these species during a post-migratory stage, to substantially eliminate said infestation and prevent its spread to beyond the locus thereof, which comprises identifying the locus of said first habitat, drilling holes in blocks, wall, slabs or other portions of the foundation of the infested building to gain access to an area consisting of said first habitat, and inserting a lethally effective amount of pesticide through said holes, whereby to exterminate any cockroaches of said species present in said area and substantially prevent further reproduction thereof.

2. The method of claim 1 in which said roaches are characterized by having an initial habitat in which they undergo early development and subsequently reproduce.

3. The method of claim 1 in which said pesticide is applied in an aqueous emulsion containing 0.5 to 2 percent pesticide based on the total solution.

4. The method of claim 3 in which said aqueous emulsion is applied in an amount of about 0.1 to 0.75 gallons per square foot of area treated.

5. The method of claim 1 in which the pesticide is selected from the group consisting of octochloro-4,7-methanotetrahydroindane, gamma isomer of benzene hexachloride, 0,0-dimethyl dithiophosphate of diethyl mercaptosuccinate and 0,0-diethyl-0-(2-isopropyl-6-methyl-4-pyrimidinyl) phosphorothioate.

* * * * *